United States Patent
Krause et al.

[11] Patent Number: 5,856,200
[45] Date of Patent: Jan. 5, 1999

[54] METHOD AND DEVICE FOR METERING LIQUIDS

[75] Inventors: Friedemann Krause, Penzberg; Sigmar Klose, Berg, both of Germany

[73] Assignee: Boehringer Mannheim GmbH, Mannheim, Germany

[21] Appl. No.: 634,366

[22] Filed: Apr. 18, 1996

Related U.S. Application Data

[63] Continuation of Ser. No. 303,018, Sep. 8, 1994, abandoned.

[30] Foreign Application Priority Data

Sep. 8, 1993 [DE] Germany .......................... 43 30 412.5

[51] Int. Cl.⁶ .................................................. G01N 33/48
[52] U.S. Cl. ...................................... 436/180; 422/82.05
[58] Field of Search .................... 436/5, 51, 164, 436/180; 422/82.05; 356/335, 336

[56] References Cited

U.S. PATENT DOCUMENTS

| | | |
|---|---|---|
| 3,164,304 | 1/1965 | Jager et al. . |
| 4,041,995 | 8/1977 | Columbus . |
| 4,328,801 | 5/1982 | Marx et al. . |
| 4,345,028 | 8/1982 | Nelson et al. . |
| 4,441,532 | 4/1984 | Hrubesh . |
| 5,278,626 | 1/1994 | Poole et al. ............................. 356/36 |

FOREIGN PATENT DOCUMENTS

| | | |
|---|---|---|
| 2 092 758 | 8/1982 | United Kingdom . |
| 2 187 549 | 9/1987 | United Kingdom . |
| 2 259 568 | 3/1993 | United Kingdom . |
| WO 96/06832 | 11/1986 | WIPO . |
| WO 90/05910 | 5/1990 | WIPO . |
| WO 93/09407 | 5/1993 | WIPO . |

OTHER PUBLICATIONS

Patent Abstracts of Japan, vol. 11, No. 68, Feb. 28, 1987.
Patent Abstracts of Japan, vol. 8, No. 265, Dec. 5, 1984.

*Primary Examiner*—Lyle A. Alexander
*Attorney, Agent, or Firm*—Nikaido, Marmelstein, Murray & Oram LLP

[57] ABSTRACT

The present invention relates to a method and a device for metering liquids, wherein the volume of a droplet of a sample liquid is determined by means of optical measuring. The liquid to be metered is brought into contact with a transfer element so that a droplet adheres to the transfer element. The transfer element and the liquid adhering thereto are illuminated from one or several directions and the resulting images are displayed on an optical sensor. The liquid volume is determined on the basis of these images. Metering is accomplished by transferring the liquid volume adhering to the transfer element into an analysis vessel.

31 Claims, 5 Drawing Sheets

METHOD AND DEVICE FOR METERING LIQUIDS

This application is a continuation of application Ser. No. 08/303,018 filed Sep. 8, 1994 now abandoned.

BACKGROUND OF THE INVENTION

1. Field of the Invention:

The present invention relates to a method and a device for metering liquids, wherein the volume of a droplet of a sample liquid is determined by means of optical measurement.

2. Description of the Prior Art:

The invention lies in the field of metering liquids for chemical and clinical analyzers. Accordingly, an expert in this field is a physicist or a physical chemist who is familiar with methods of metering liquids which are currently known in the prior art and also with optical devices.

In prior art there exist methods where liquids are dispensed by high-precision pistons, so-called diluters. Liquid volumes that are within the range of a few microliters can be metered with so-called micropipettes. Another method of metering liquids in the microliter range is described in German Patent Application P 4243247.2. In this method, the liquid level in a capillary tube is detected by means of an electro-optical element and varying liquid levels in the capillary tube are converted into metered volumes. This method addresses the optical detection of the liquid meniscus to ensure sufficiently exact metering.

3. Summary of the Invention:

It is, hence, a drawback of the methods known in prior art that only liquid amounts greater than approx. 1 µl can be metered. Moreover, the instrument parts which contact the liquid are relatively complex and expensive, a fact which calls for multiple usage rather than disposable units.

It was, hence, an object of the invention to provide a method and a device for metering liquids, which also allows the reliable and precise metering of liquid volumes that are smaller than 1 µl. Another object of the invention was to eliminate contamination of the metering device.

The method of the invention for metering liquids comprises the following steps:

a) a contact step where the transfer element is brought into contact with the liquid such that a droplet of the liquid adheres to the transfer element, b) an imaging step where the droplet and at least a part of the transfer element are illuminated and where an optical system produces at least one picture of the droplet and of a part of the transfer element on an optical sensor, c) an optical measuring step where contours of the droplet are determined based on the at least one picture produced on the optical sensor and where the volume of the droplet is calculated from the so determined contours, d) a transfer step where the droplet adhering to the transfer element is transferred into an analysis vessel.

Moreover, the invention relates to a system for metering liquids including a unit for illuminating elements, an adjusting device, a detection device, an evaluation device and a transfer device where the volume of a droplet of the liquid is optically determined.

The method of the invention addresses the metering of very minute amounts of liquid ranging from a few nanoliters up to microliters. Metering as understood in this invention is not the release of a predetermined amount of liquid into an analysis vessel, but rather the addition of an amount of liquid which can essentially not be predetermined, but can be determined with great accuracy before it is transferred into the analysis vessel. This does usually not restrict the possibilities of analyzing liquids. With respect to the available amount of sample, known analysis methods are relatively flexible. However, the accuracy of the analysis directly relates to the accuracy at which the metered amount of sample can be determined.

In the method of the invention, liquid to be metered is brought into contact with a transfer element. This can be done, for example, by immersing the transfer element into the liquid to be metered and then taking it out again. The liquid adhering to the transfer element is the sample volume to be added into the analysis vessel. The liquid could, however, also be directly added onto the transfer element to which it then adheres due to adhesive and/or gravitational forces.

Depending on these different possibilities of bringing liquid into contact with the transfer element, the latter can assume numerous shapes and sizes. The transfer element can, for example, have the form of a rod which is immersed into the liquid to be metered with liquid in the form of a droplet then adhering to its front side. The amounts of liquid to be metered can be changed by varying the form of the front part of the transfer element. Further, the amount of adhering liquid depends upon the surface properties of the transfer element as well as the properties of the liquid, e.g. its viscosity. In a preferred embodiment, the rod-like transfer element is a fiber. Possible materials include glass, plastics such as polyethylene, polypropylene, polymethylmetacrylate, polyethylenetherephthalate, and metals and alloys. The transfer element which is particularly suitable in accordance with the invention is obtained when the circumferential surface of the rod-like body exerts only minor adhesive forces onto the liquid to be metered, whereas the front surface should exhibit good adsorptive properties. With such an embodiment given, the droplet adhering to the front surface of the transfer element does not adhere to the walls of the transfer element which would render the determination of the volume more complicated. Transfer elements in accordance with the invention which have the form of a small rod can be obtained by reducing the size of longer fibers by means of cutting, melting or in any other way. It is particularly preferred to provide the transfer element with the coating as described, for example, by the Fraunhofer Institute (Material Science Monographs, 67, page 203 et seq., 1991), for example. If the material used for the transfer element is one that exhibits strong adsorptive forces with respect to the sample liquid, the outside of the transfer element can be coated with a liquid-repellent film. If such a fiber-like transfer element is separated, the cut edge thereof has a surface with good adsorptive capacities (usually hydrophilic), whereas the circumferential surface exhibits minor adsorptive forces (usually hydrophobic).

In another preferred embodiment, the transfer element has a planar surface element which appears larger than the droplet of liquid to be metered. In accordance with the invention, it is possible to use foils made of plastics, glass, or metal. Advantageously, the materials used include those that are at least partly transparent to light. It is also advantageous that the surface of the transfer element be liquid-repellent to support the formation of spherical droplet and to avoid bleeding of the liquid on the surface.

Physically, hydrophobic surface material can be recognized in that aqueous droplets of liquid form a great wetting angle thereon. Plastics that are suitable for this application include polyvinylidene fluoride (Teflon), polyethylene, polypropylene, and polymethylmetacrylate. Surfaces with minor hydrophobic properties can be impregnated by coating with organosilanes, for example.

In accordance with the invention, the volume of liquid adhering to the transfer element is determined by optically measuring the contours of the adsorbed liquid. It is preferred to first measure the contours of the transfer element without any liquid, and to then include in the calculation the volume of the transfer element covered by the liquid.

In order to carry out the optical measurement, the transfer element is illuminated and after passing the transfer element, the beam of light is directed onto an optical sensor. As the sample volumes used in accordance with the invention and, hence, the droplets of liquid are within the range of millimeters and below, the illumination is subject to heavy diffraction. In order to determine the volume, the contours of the droplet must be determined with great accuracy which requires that the diffraction be included in the determination of the contours.

Figure 1:
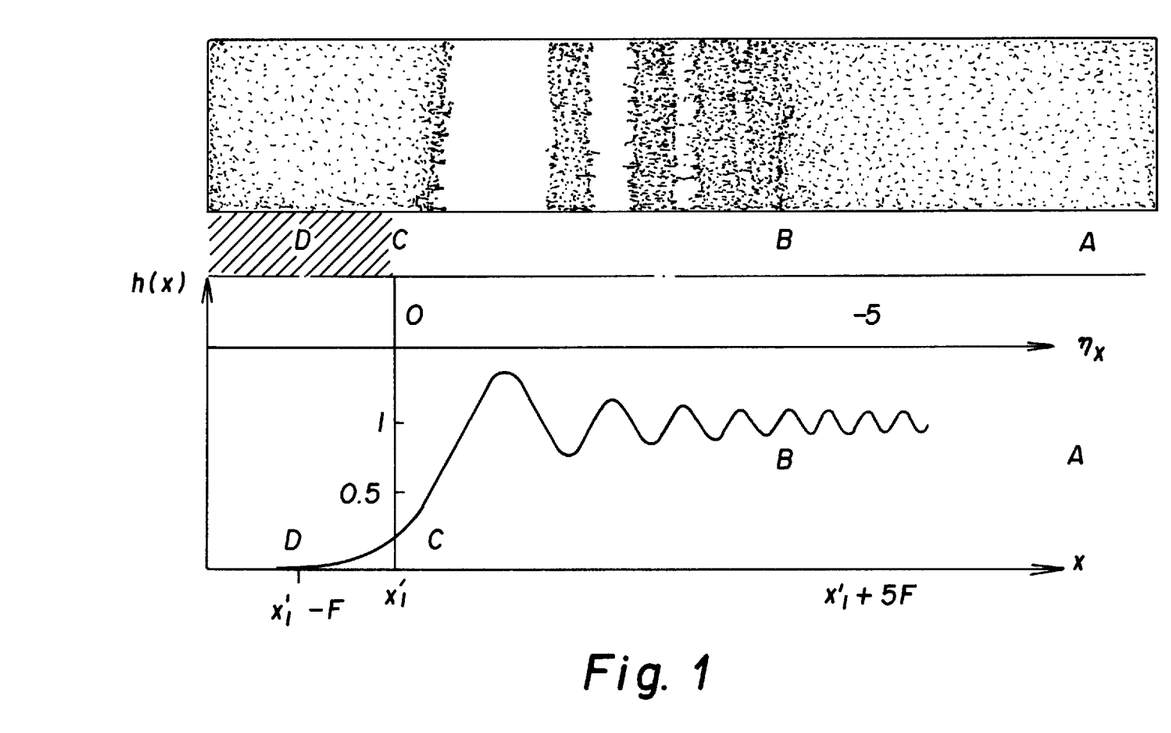

FIG. 1 shows how light is diffracted at an edge. From the brightness function h(x) it can be recognized that the physical edge (site $x'_1$) is at approximately 25% of the brightness for the great values of x (reference brightness). The physical edge can, therefore, be determined by first determining the reference brightness, i.e. the maximum brightness possible, and, thereon, the site where the brightness corresponds to 25% of the reference brightness. In the practice, however, it is more advantageous to calibrate the determination of the physical edge. To achieve this, a body with known and exactly defined contours is placed into the beam of light. The percentage of brightness at the edge can be determined for a given measurement arrangement by measuring the brightness function. Any change to the measurement arrangement (strength of illumination, direction of beams) usually requires recalibration. When bodies with unknown contours are measured, the brightness function at the physical edge is determined and evaluated based upon the previous calibration. In a simple threshold process, the one point of the curve, which according to its percentage of brightness based upon the reference brightness corresponds to the edge, is associated with the edge of the object.

In a more complex evaluation procedure, a larger part of the brightness curve is included in the calculation, ranging, for example, from $x'_1-F$ up to $x'_1+5F$. The measured part of the function is approximated in a spline function. The coefficient of the spline function is determined in a comparison with the physical model of the brightness function of the points $x'_1$, i.e. the physical edge.

In order to determine the volume of droplet, the brightness function must be determined at numerous different points of the droplet. Once the contours of the droplet and those of the contiguous transfer element have been determined, the volume of the droplet can be calculated. This can be done, for example, based upon the model of a round or elliptic droplet. In a very simple model, it can be assumed that the droplet adhering to the transfer element has the form of a spherical segment. In this case, the determined contours of the droplet allow conclusions with respect to the curvature of the surface of the sphere and, hence, its radius. The volume of the droplet can then be mathematically concluded from the volume of the corresponding spherical segment. In similar simple models, the droplet adhering to the transfer element is considered to be a segment of an ellipsoid. With complicated computerized methods, the surface of the droplet is first scanned and, based upon the reference points, the contour is determined in an interpolation function. The actual determination of the volume can then be carried out by filling the space below the contour of the droplet with polyhedrons.

With the latter method, it is also possible to account for irregularities on the surface of the transfer element which contacts the droplet.

In addition to these mathematically complex procedures, it is also possible to provide technical solutions for the determination of the volume by bringing known volumes onto the transfer elements and determining the resulting contours. These measurements can be used to establish calibration curves to determine unknown volumes.

Following the determination of the volume, the transfer element with the sample droplet is as soon as possible transferred into an analysis vessel or otherwise analyzed. Generally, the time interval between contacting transfer element and sample and the beginning of the analysis should be kept as short as possible to avoid evaporation of the liquid. For a correct analysis, only the time between contact of transfer element and sample and the determination of the volume is essential, as all subsequent concentration calculations are based on the volume measured. Evaporation after the determination of the volume is in most cases irrelevant with respect to the concentration calculation as the parameters that are relevant for the clinical analysis have a high vapor pressure. The amount of analyte present in the sample droplet, hence, remains constant.

Experience has shown that for sample volumes between 400 nl and 1 $\mu$l, measurement is possible within 3 to 5 seconds after collecting the sample in order to keep the error rate in the determination of the concentration due to evaporation smaller than 3%. When all ambient conditions are known, especially air pressure, temperature, and humidity, the amount evaporating over a given time can either be empirically determined or be calculated. A description of a calculation of the evaporation of small droplets can be found in Peiss, C. N. *J. Appl. Phys.* 65(12)15. The empirically or mathematically determined amount of evaporated substance is used to correct the droplet volume determined in accordance with the invention to increase the accuracy of the analysis.

Another possibility of increasing the accuracy of the metering is to reduce the evaporation of the sample droplet. This can be accomplished by reducing the ambient temperature and, especially, by increasing the ambient humidity.

The invention further comprises a system for metering liquids having the following elements.

a) a transfer element with at least one droplet of liquid to which the at least one droplet of a liquid adheres due to adhesive and/or gravitational forces, b) an illumination unit which has at least one light source and which can have an arrangement of lenses, mirrors, and diaphragms, c) an adjusting device to position the transfer element and allowing movement of the transfer element in at least one spatial direction within the light path of the illumination unit, d) a detection device to detect light after this light has passed the transfer element and which can also have an arrangement of lenses, mirrors, and diaphragms, e) an evaluation device to determine the contours of at least one droplet of liquid with the aid of signals from the detection unit and then calculates the volume of a droplet of liquid, f) a transfer device to transfer the element with at least one droplet of liquid into an analysis vessel.

A system of the invention has an illumination unit to illuminate the transfer element and the droplet of liquid adhering thereto. Possible sources of light are conventional lamps, e.g. incandescent lamps or halogen lamps. In a preferred manner, these lamps are operated such that a constant degree of brightness is maintained. In an advantageous embodiment, a bundle of parallel beams is generated from the light of the light source via a lens system. This bundle of beams is used to illuminate the transfer element together with the droplets adhering thereto. With a second lens system, an image of the droplet and the adjacent transfer element is produced on a sensor. A reproducible and, therefore, particularly advantageous arrangement is obtained if the droplet of liquid is in the focus of the lens system which produces its image. This can be accomplished with the aid of an adjusting device.

The image of the droplet is projected on an optical sensor which allows a one-dimensional, preferably two-dimensional evaluation of the brightness. Suitable means are so-called vidikons or semi-conductor image sensors. Preferably, so-called CCD arrays (charged coupled devices) are used as these are commercially available at relative low prices and ensure a high resolution of the image.

Each sensor is connected to a computer system which generates a one- or two-dimensional picture from the signals of the element of the sensors.

With the currently described method it is possible to obtain one- or two-dimensional projections of the droplet. To determine the volume, however, it is necessary to have a spatial structure of the droplet. The adjacent transfer element is, therefore, used to illuminate the droplet from several spatial directions. This can be achieved by splitting the light of the source by means of a beam splitter (e.g. prism), then redirecting it via mirror systems and directing it onto the droplet from different spatial directions. In a rod-like transfer element, the droplet is preferably illuminated in two or three directions perpendicular to the axis of the transfer element. For a droplet which is located on a flat transfer element, the preferred illumination runs parallel and perpendicular to the surface of the transfer elements.

Once the light beams have passed the droplet, they can be directly guided onto several sensors or, preferably, combined via mirror systems and directed onto one single sensor. When one single sensor is used, it is preferred to successively activate the individual light beams and to deactivate the remaining light beams, respectively.

BRIEF DESCRIPTION OF THE DRAWINGS

The following figures are intended to clarify the invention:

FIG. 1

Theoretical course of the brightness function with diffraction at an edge

FIG. 2a

Rod-like transfer element with and without droplet

FIG. 2b

Rod-like transfer element with droplet

FIG. 3

Device for optically determining the volume with a rod-like transfer element

FIG. 4

Device for optically determining the volume with a planar transfer element

FIG. 5

Determining the volume of elliptic droplets

DETAILED DESCRIPTION OF THE PREFERRED EMBODIMENTS

Figure 2A:
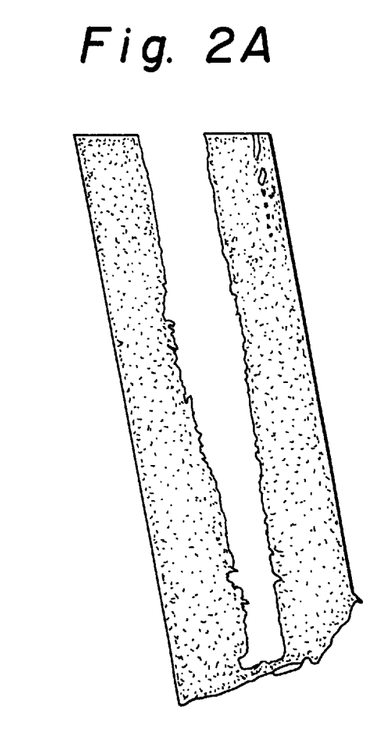
Figure 2B:
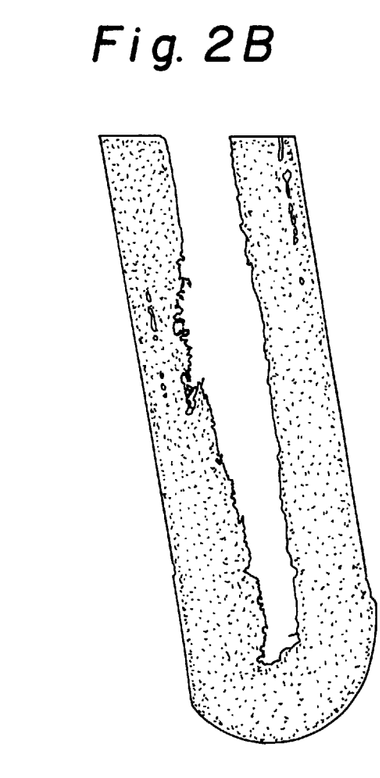

FIG. 2a shows a glass fiber without sample liquid. It can be clearly seen that the front side shows surface irregularities. FIG. 2b shows the same glass fiber after it had been brought into contact with sample liquid. The liquid adhering to it assumes the shape of a spherical segment. In this case, however, the structure of the break edge of the glass fiber must be accounted for in the determination of the volume.

Figure 3:
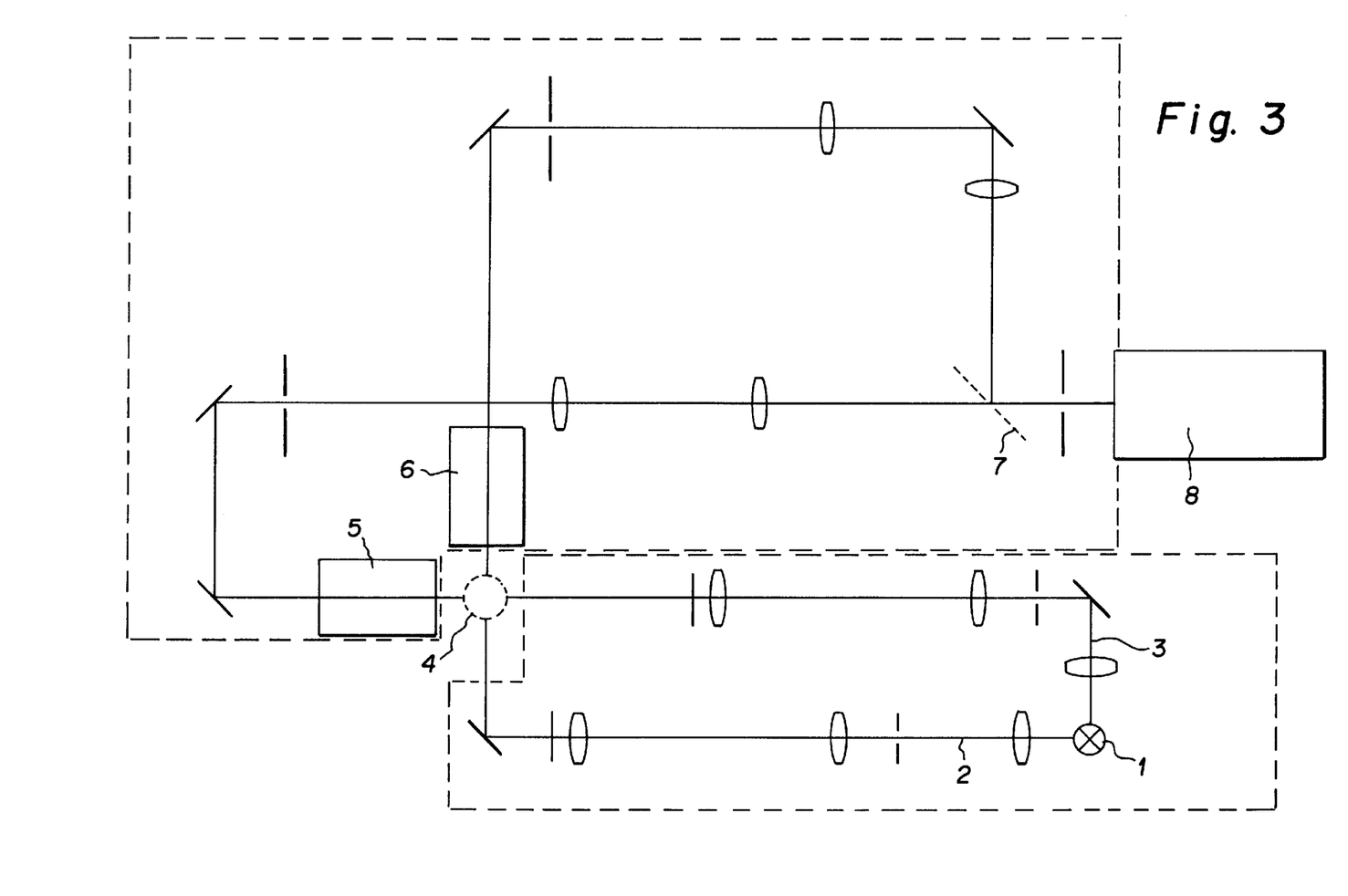

FIG. 3 is a diagrammatic representation showing the structure of a system for measuring sample volumes of droplets using a rod-like transfer element. The light of lamp (1) is split into two beams (2) and (3) with each beam being directed onto the sample adhering to the transfer element (4) via a system of lenses, diaphragms, and mirrors. The axis of a rod-like transfer element runs perpendicularly to the drawing surface. The light beams (2) and (3) consequently illuminate the sample droplets from two perpendicular directions which in turn run perpendicularly to the axis of the transfer element. The illuminated sample droplet is located in the focus of the lens systems (5) and (6) by which it is imaged in such a way that a sharp picture is generated on the CCD-camera (8). The bundles of beams emerging from the lens systems (5) and (6) pass through an arrangement of mirrors, diaphragms, and lenses. The semi-permeable mirror (7) directs the partial beams onto the CCD-camera (8).

Figure 4:
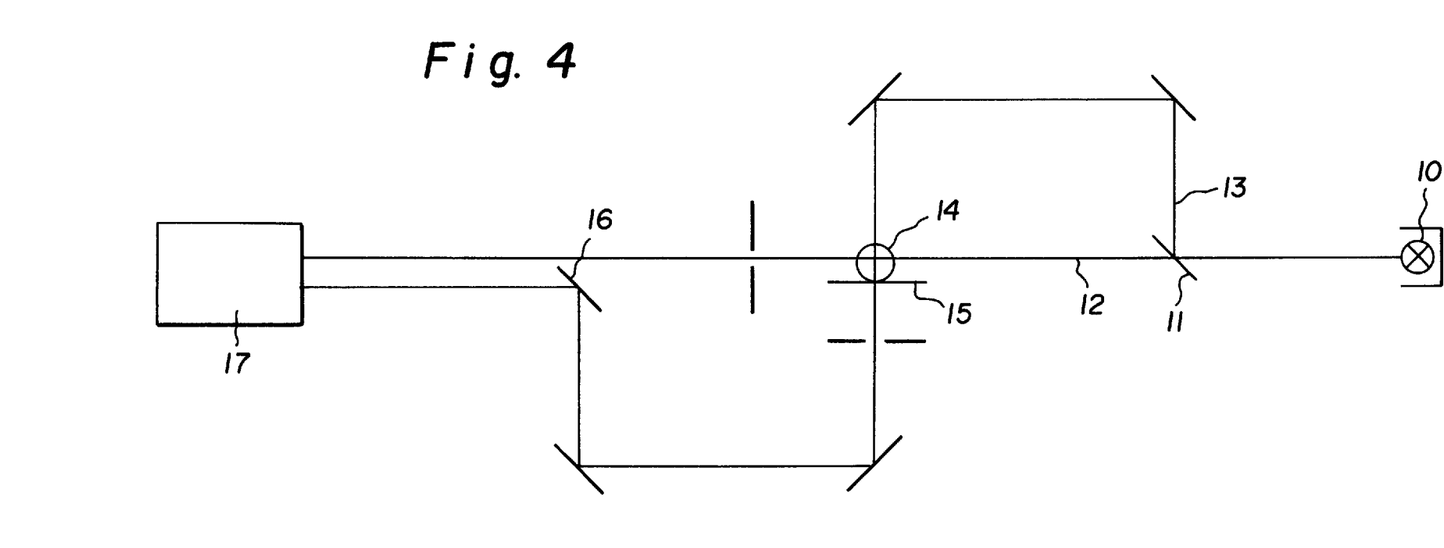

FIG. 4 shows a system for determining the volume of a droplet on a support. The light emerging from the source (10) is split into two partial beams (12) and (13) by means of a beam splitter (11). The sample liquid (14) has the form of a droplet on the support (15). The light beam (12) illuminates the sample droplet from the side, i.e. parallel to the flat sample carrier (15). Beam (13) illuminates droplet (14) from top and traverses the light-permeable support (15). After beams (12) and (13) have passed the sample droplet, a common image is produced on a sensor (17) by means of a semi-permeable mirror (16).

Figure 5:
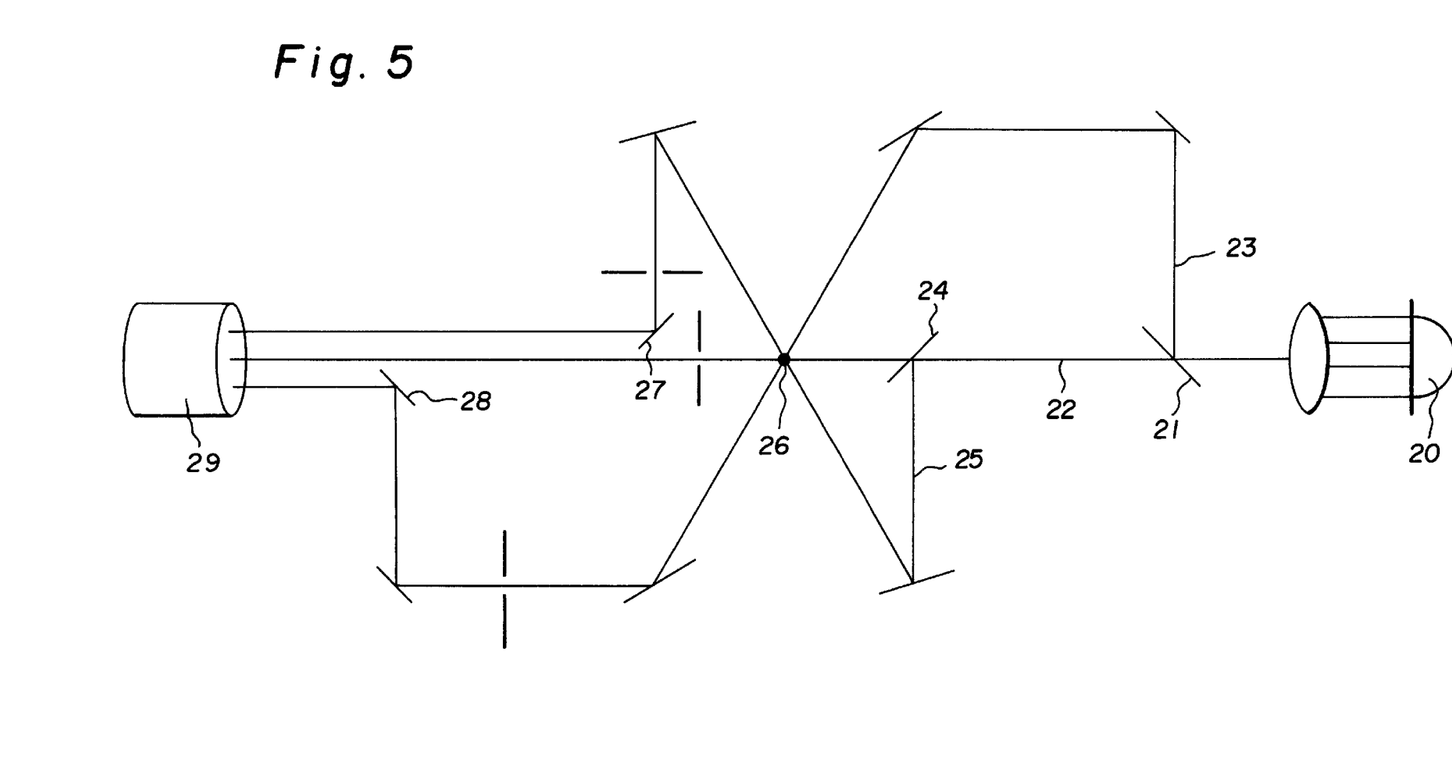

FIG. 5 shows an arrangement for measuring ellipsoid sample droplets on a rod-like transfer element. When the transfer elements are produced, e.g. by cutting a thread, the cut will produce edges which do not have an ideal circular form, but instead are elliptical. The sample droplet adhering to such a transfer element will also assume an elliptical shape. It is also possible that a droplet located on a circular transfer element assumes a distorted shape. Accordingly, when a droplet is applied onto an even transfer element, the droplet may not assume an ideal circular shape, but will be subject to contortion. In order to determine the larger and the smaller main axis of an ellipse, it is necessary to illuminate the sample droplets in 3 directions which are located on one plain.

The light emitted by the light source (20) is focused through a convex lens and directed onto the beam splitter (21) which separates the beams into bundles (22) and (23). Bundle (22) is again split by the beam splitter (24) to produce another bundle (25). Beams (22), (23), and (25) illuminate a rod-like transfer element (26) and the sample droplet adhering thereto perpendicularly to the axis of the transfer element. In FIG. 5, the axis of the rod-like transfer element is a aligned perpendicularly to the axis of the drawing. The bundles are located on one plain (the plain of drawing) and form an angle of 60° with respect to one another. The semi-permeable mirrors (27) and (28) combine the bundles of light to direct them onto sensor (29).

| List of reference numerals | |
| --- | --- |
| (1) | Lamp |
| (2), (3) | Light beams |
| (4) | Transfer element |
| (5), (6) | Lens systems |
| (7) | Mirror |
| (8) | CCD camera |
| (10) | Light source |
| (11) | Beam splitter |
| (12), (13) | Partial beams |
| (14) | Sample liquid |
| (15) | Support |
| (16) | Semi-permeable mirror |
| (17) | Sensor |
| (20) | Light source |
| (21) | Beam splitter |
| (22), (23) | Bundle of beams |
| (24) | Beam splitter |
| (25) | Bundle of beams |
| (26) | Transfer element |
| (27), (28) | Semi-permeable mirrors |
| (29) | Sensor |

The following examples are intended to further illustrate the invention:

EXAMPLE 1

A small droplet of glass which was first measured with a micrometer screw was attached to a glass rod by means of melting. The arrangement was then placed into the measuring device as depicted in FIG. 3. To compare the various evaluation procedures, pictures of the droplet were electro-optically analyzed. The pictures were evaluated with a spline function procedure and a threshold procedure. When the spline function procedure was applied, the information of the diffraction picture was evaluated as described above, whereas in the threshold procedure only the site where the brightness corresponds to 25% of the reference brightness was determined. Whereas measurement with a micrometer screw gives the maximum of the diameter, electro-optical procedures require the determination of the contours of the droplet in various layers to finally obtain the diameter. Table 1 shows the results for measurement series carried out with two droplets of glass of different sizes. The pictures were taken with a CCD-camera having pixel dimensions of 7×7 $\mu$m. An interpolation procedure was used to increase the resolution to elements with a size of approximately 1.8×1.8 $\mu$m. The table shows that in the electro-optical procedure, the diameter of the glass droplets could be easily reproduced. Only measurement 7 is outside the acceptable range as this measurement was carried out at a very low brightness.

EXAMPLE 2

Metering a sample volume with a rod-like transfer element

The transfer element is attached to a measuring device (according to FIG. 3) such that an exact picture of the end of the rod is produced on a CCD-camera. The transfer element can, for example, be a piece of a glass fiber or a piece of a thin metal wire coated at its outside. With a corresponding device, a sample cuvette is brought to the transfer element while the rod is immersed into the sample liquid. A liquid level sensor attached to the measuring device is used to monitor the immersion depth of the rod in the liquid. After removing the sample cuvette, the transfer element with the liquid adhering thereto is immediately optically measured in accordance with the invention to avoid evaporation errors as far as possible. Subsequently, the rod is added into a reaction cuvette together with the sample and after calculation of the sample volume, the corresponding amount of reagent and buffer solution is added.

TABLE I

| | Spline function process Diameter | | Threshold process Diameter | | Micrometer screw |
| --- | --- | --- | --- | --- | --- |
| No. | In pixel | In $\mu$m | In pixel | In $\mu$m | diameter in $\mu$m |
| 1 | 205.59 | 367.11 | 206.57 | 368.86 | 368.3 |
| 2 | 205.82 | 367.52 | 206.85 | 369.36 | 368.3 |
| 3 | 206.11 | 367.80 | 207.18 | 369.71 | 368.3 |
| 4 | 206.69 | 368.64 | 207.60 | 370.26 | 368.3 |
| 5 | 205.16 | 360.25 | 206.11 | 361.95 | 359.3 |
| 6 | 205.83 | 361.43 | 206.25 | 362.19 | 359.3 |
| 7 | 197.63 | 347.03 | 192.73 | 338.42 | 359.3 |

We claim:

1. A method of metering a liquid to be used in an analysis, said method comprising the steps of:
    a) contacting a transfer element with the liquid to cause a droplet of the liquid to adhere to and cover an end of the transfer element;
    b) illuminating the droplet and at least a part of the transfer element to produce at least one picture of the droplet and of a part of the transfer element on an optical sensor;
    c) determining the contours of the droplet on the transfer element from the at least one picture produced on the optical sensor, and calculating the volume of the droplet from the determined contours; and
    d) transferring the droplet adhering to the transfer element to an analysis vessel,
wherein the transfer element is a solid rod-like body having at least one front side and one circumferential surface, and wherein the droplet adheres to the front side of the transfer element.

2. Method of claim 1, wherein the droplet and at least a part of the transfer element are illuminated in at least two spatial, non parallel directions to produce at least two images of the droplet and a part of the transfer element, which at least two images are used to calculate the volume of the droplet.

3. Method according to claim 1, wherein the volume of the droplet is between 10 and 500 nl.

4. Method of claim 1, including the step of recording the at least one image of the droplet and a part of the transfer element with a CCD-camera.

5. Method of claim 1, wherein the droplet and at least a part of the transfer element are illuminated by a light source, with the optical path between the light source and the optical sensor being modified by the use of lenses, mirrors and diaphragms.

6. Method of claim 1, wherein the sample volume is between 400 nl and 1 $\mu$l, and the production of a picture of the droplet and the part of the transfer element on the optical sensor is within 3 to 5 seconds after the contact step.

7. Method of claim 1, wherein the droplet is illuminated from a light source, and the method includes the additional steps of splitting the light from the light source by means of a beam splitter, and redirecting the light on the droplet from different spatial directions.

8. Method of claim 1, wherein the contours of the droplet and a part of the transfer element are determined from the at least one image with the aid of a spline function using the diffraction pattern.

9. Method of claim 1, wherein the optical sensor has a given light sensitivity level, and the droplet and at least a part of the transfer element are illuminated with light of a brightness which is at least 10-fold greater than the light sensitivity level.

10. A method of metering a liquid as recited in claim 1, said method comprising initial steps of:
   illuminating the transfer element to produce at least one picture of a part of the transfer element on an optical sensor, and determining contours of the part of the transfer element from the at least one picture.

11. Method according to claim 1, wherein the rod-like transfer element has a circumferential surface to which the liquid essentially does not adhere, and a front side to which the liquid does adhere.

12. A method according to claim 11, wherein said circumferential surface is hydrophobic and wherein said front side is hydrophilic.

13. Method of claim 1, wherein the contours of the droplet and a part of the transfer element are determined from the at least one image by the use of a brightness cut-off value.

14. Method of claim 13, wherein the brightness cut off value is approximately 25 percent of a reference brightness which is the maximum brightness of a light source illuminating the droplet and at least a part of the transfer element.

15. A method of metering a liquid to be used in an analysis, said method comprising the steps of:
   a) contacting a liquid impermeable transfer element with the liquid to cause a droplet of the liquid to adhere to the transfer element;
   b) illuminating the droplet and at least a part of the transfer element to produce at least one picture of the droplet and of a part of the transfer element on an optical sensor;
   c) determining the contours of the droplet on the transfer element from the at least one picture produced on the optical sensor, and calculating the volume of the droplet from the determined contours; and
   d) transferring the droplet adhering to the transfer element to an analysis vessel, wherein the transfer element is a planar surface element of a size which is greater than the diameter of the droplet.

16. Method of claim 15, wherein the wetting angle formed between the droplet and the planar surface element of the transfer element is greater than 90°.

17. A method of metering a liquid as recited in claim 15, said method comprising initial steps of:
   illuminating the transfer element to produce at least one picture of a part of the transfer element on an optical sensor, and determining contours of the part of the transfer element from the at least one picture.

18. A method according to claim 15, wherein said step of illuminating the droplet and at least a part of the transfer element includes irradiation of light through a light-permeable part of the transfer element.

19. A system for metering liquids comprising:
   a) a transfer element to which at least one droplet of liquid adheres due to adhesive and/or gravitational forces, said transfer element comprising a solid rod-like body:
   b) an illumination unit including at least one light source, for illuminating the droplet and at least part of the transfer element;
   c) adjusting means for supporting the transfer element and for allowing movement of the transfer element in at least one spatial direction within a light path of the illumination unit;
   d) detecting means for detecting light after the light has passed the transfer element, and for producing at least one picture of the droplet and a part of the transfer element;
   e) evaluation means for determining the contours of the at least one droplet of liquid with the aid of signals from the detection means, and for calculating from the contours so determined the volume of the at least one droplet of liquid; and
   f) transfer means for transferring the element with at least one droplet of liquid thereon to an analysis vessel.

20. System of claim 19, wherein the illumination unit has at least two bundles of beams illuminating in non-parallel spatial directions the at least one droplet adhering to the transfer element.

21. System of claim 19, wherein the detection means is a CCD-camera equipped with a system including lenses, mirrors and diaphragms.

22. System of claim 19, wherein the adjusting means positions the least one droplet of liquid in the focus of a lens system, and projects at least one image of the at least one droplet of liquid on an optical sensor.

23. System of claim 19, wherein the detecting means has a given level of sensitivity to light, and the illumination source illuminates the transfer element with light having a brightness which is at least 10-fold greater than the said light sensitivity level.

24. System of claim 19, wherein the evaluation means uses threshold value procedures or spline function procedures based on the signals of the detection means to determine the contours of the at least one droplet of liquid, which then permit the calculation of the volume of said at least one droplet of liquid.

25. System of claim 24, wherein the evaluation means uses threshold value procedures based on a brightness cut-off value, and the brightness cut-off value is approximately 25% of a reference brightness which is the maximum brightness of the light source.

26. A system for metering liquids comprising:
   a) a transfer element to which at least one droplet of liquid adheres due to adhesive and/or gravitational forces, wherein the transfer element has a planar surface element which is of a size greater than the diameter of the droplet;
   b) an illumination unit including at least one light source, for illuminating the droplet and at least part of the transfer element;
   c) adjusting means for supporting the transfer element and for allowing movement of the transfer element in at least one spatial direction within a light path of the illumination unit;
   d) detecting means for detecting light after the light has passed the transfer element, and for producing at least one picture of the droplet and a part of the transfer element;
   e) evaluation means for determining the contours of the at least one droplet of liquid with the aid of signals from the detection means, and for calculating from the contours so determined the volume of the at least one droplet of liquid; and
   f) transfer means for transferring the element with at least one droplet of liquid thereon to an analysis vessel.

27. A method of determining the volume of a droplet of a liquid, said method comprising:
   a) contacting a transfer element with the liquid to cause a droplet of the liquid to adhere to and cover an end of the transfer element, b) illuminating the droplet and at least a part of the transfer element to produce at least one picture of the droplet and of a part of the transfer element on an optical sensor, c) determining the contours of the droplet from the at least one picture produced on the optical sensor, and calculating the volume of the droplet from the so determined contours, wherein said transfer element comprising a solid rod-like body having at least one front side and one circumferential surface, and wherein the droplet adheres to the front side of the transfer element.

28. A method of metering a liquid to be used in an analysis, said method comprising the steps of:

a) contacting a transfer element with the liquid to cause a droplet of the liquid to adhere to the transfer element, wherein said transfer element is formed such that the liquid does not penetrate the transfer element;

b) illuminating the droplet and at least a part of the transfer element to produce at least one picture of the droplet and of a part of the transfer element on an optical sensor;

c) determining the contours of the droplet on the transfer element from the at least one picture produced on the optical sensor, and calculating the volume of the droplet from the determined contours; and d) transferring the droplet adhering to the transfer element to an analysis vessel, wherein the transfer element is a solid rod-like body having at least one end and one circumferential surface, and wherein the droplet adheres to and covers the at least one end of the transfer element.

29. A method according to claim 28, wherein said step of illuminating the droplet and at least a part of the transfer element includes irradiation of light through a light-permeable part of the transfer element.

30. A method of metering a liquid to be used in an analysis, said method comprising the steps of:

a) contacting a transfer element with the liquid to cause a droplet of the liquid to adhere to the transfer element, wherein said transfer element is formed such that the liquid does not penetrate the transfer element;

b) illuminating the droplet and at least a part of the transfer element to produce at least one picture of the droplet and of a part of the transfer element on an optical sensor;

c) determining the contours of the droplet on the transfer element from the at least one picture produced on the optical sensor, and calculating the volume of the droplet from the determined contours; and d) transferring the droplet adhering to the transfer element to an analysis vessel, wherein the transfer element is a liquid impermeable planar support element, and wherein the droplet adheres to a surface of the planar support element, and wherein the planar support element has a size which is greater than the diameter of the droplet.

31. A method of determining the volume of a droplet of a liquid said method comprising:

a) contacting a transfer element with the liquid to cause a droplet of the liquid to adhere to the transfer element, b) illuminating the droplet and at least a part of the transfer element to produce at least one picture of the droplet and of a part of the transfer element on an optical sensor, c) determining the contours of the droplet from the at least one picture produced on the optical sensor, and calculating the volume of the droplet from the so determined contours, wherein said transfer element comprises a liquid impermeable planar surface element of a size which is greater than the diameter of the droplet, and wherein the step of determining the contours of the droplet occurs based upon the droplet when it is adhered to the transfer element.

* * * * *